United States Patent [19]

Fox

[11] Patent Number: 4,836,452

[45] Date of Patent: Jun. 6, 1989

[54] EFFICIENT ARTIFICIAL SMOKE GENERATOR

[76] Inventor: Jim Fox, 5606 Park Oak Pl., Hollywood, Calif. 90068

[21] Appl. No.: 185,514

[22] Filed: Apr. 25, 1988

[51] Int. Cl.$^4$ .............................................. A61M 11/06

[52] U.S. Cl. .................................... 239/338; 239/14.1; 239/370; 239/74; 261/119.1

[58] Field of Search ..................... 239/14.1, 102.1, 338, 239/370, 74, 136, 129; 261/119.1

[56] References Cited

U.S. PATENT DOCUMENTS

| | | | |
|---|---|---|---|
| 1,176,669 | 3/1916 | Endres et al. | 239/338 X |
| 1,897,378 | 2/1933 | Hinkle | 239/338 |
| 2,951,644 | 9/1960 | Mahon | 239/338 X |
| 3,244,641 | 4/1966 | Durr et al. | 239/129 X |
| 3,472,455 | 10/1969 | Johnson | 239/338 X |
| 3,652,015 | 3/1972 | Beall | 239/338 |
| 3,899,129 | 8/1975 | Fukuta | 239/14.1 |
| 4,074,666 | 2/1978 | Pierce et al. | 261/119.1 X |
| 4,620,670 | 11/1986 | Hughes | 239/338 |

FOREIGN PATENT DOCUMENTS

| | | | |
|---|---|---|---|
| 123229 | 11/1944 | Australia | 239/338 |

*Primary Examiner*—Andres Kashnikow
*Assistant Examiner*—Patrick N. Burkhart
*Attorney, Agent, or Firm*—Poms, Smith, Lande, & Rose

[57] ABSTRACT

An artificial fog generator device is provided with air jet pipes, an oil bath, filtering screens, and an enclosing housing to include all of these elements, and outlet channels for directing the generated cloud of oil bubbles from the housing, and an air compressor that feeds high pressure air into the spraying pipes. A much more efficient generator of fine oil bubbles is achieved by locating the air jet pipes directly above the surface of the oil bath. The compressed air is fed into the pipes that are located directly above the oil bath and high pressure air jets spraying into the oil bath cause a cloud of fine oil bubbles to fly out of the oil bath. The generated oil bubbles than pass through the filtering screens and are then directed out of the housing through the outlet channels. The fog or smoke generator housing may be portable, and have a carrying handle, and may contain the air compressor, and a power supply and battery to power the air compressor.

17 Claims, 4 Drawing Sheets

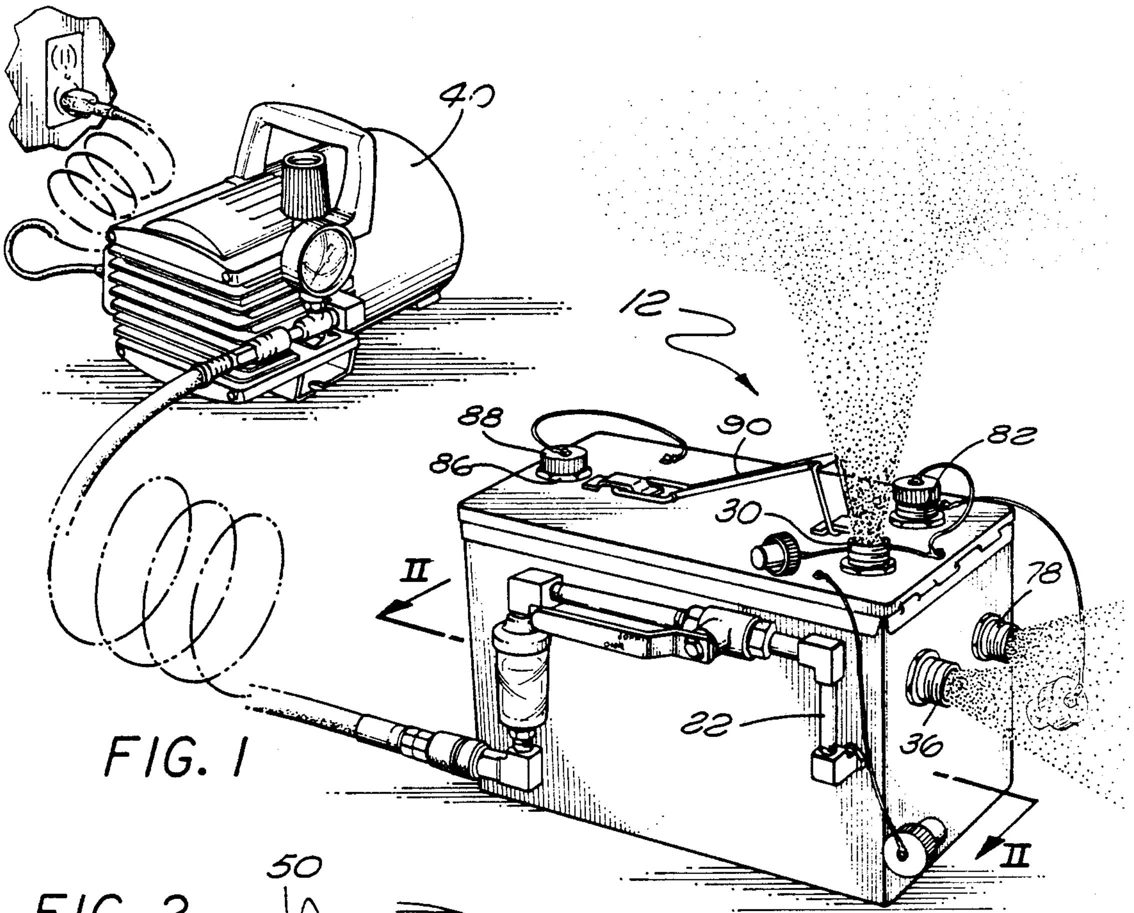
FIG. 1
FIG. 2
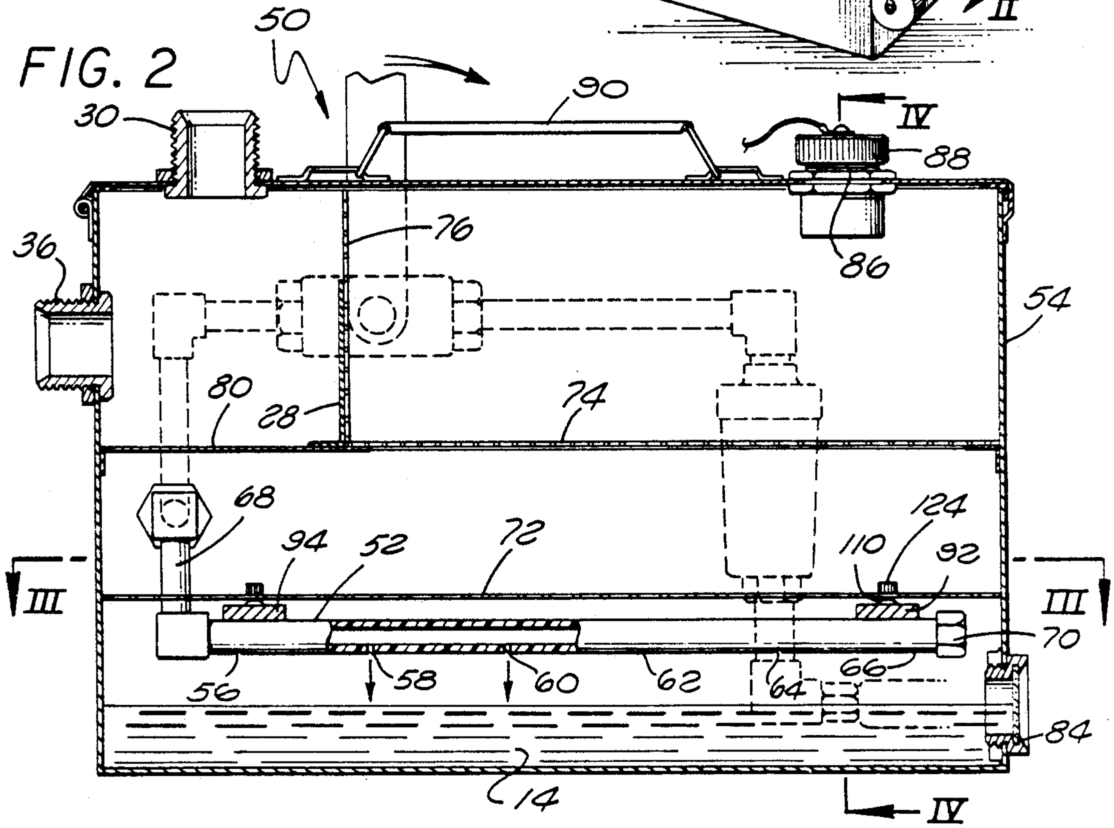

EFFICIENT ARTIFICIAL SMOKE GENERATOR

FIELD OF THE INVENTION

This invention relates to artificial smoke or fog generators.

BACKGROUND OF THE INVENTION

In the field of special effects in motion pictures, artificial smoke or fog generators have been used for generating artificial clouds of smoke or fog. Traditionally, artificial fog was produced by spraying or atomizing pure mineral oil into the surrounding atmosphere. Another type of fog has been made by percolating high pressure air through an oil tank. Some of the historical methods of generating artificial fog are described in the book *Special Effects in Motion Pictures,* which is a text which discusses the subject. With respect to the above-mentioned methods of generating artificial fog, the book explains: "both methods were long since discarded by the studios, because of the heavy oil deposits which frequently ruined wardrobe articles and usually rendered sets dangerously oily and slippery."

As noted above, traditional fog producing machines generate a heavy oil deposit in the surrounding environment. The heavy oil deposit is produced because these machines generate a significant amount of relatively large oil bubbles. These machines normally use a fog nozzle immersed in a large oil bath. A strong pump is used to produce a strong stream of air that is fed to the immersed nozzle. While the nozzle is immersed in the oil bath, the stream of air bursts out of the nozzle and creates a significant amount of large and fine oil bubbles.

Recently, attempts have been made to filter out the larger oil bubbles and allow only the finer oil bubbles to be emitted from these machines. Although the more recent artificial smoke generators produce somewhat finer oil bubbles, these machines are still very large, inefficient, and costly to rent and maintain.

Even the very recent models of artificial smoke generators which have been commercially available are normally transported in a truck. Delivery or other transportation costs significantly add to the cost of renting the machines. In addition, these large machines consume substantial quantities of power when in operation, because a large air compressor is normally used for feeding a strong stream of air into the fog nozzle. Further, the rental fee is relatively high due to the high maintenance cost, size and complexity of the machines.

In addition most of these machines require maintenance by both the user and vendor. For example, the user is normally required to change some of the oil filters inside the machine.

Accordingly, the principal object of the present invention is to provide a small, efficient, inexpensive and maintenance-free artificial fog generator that produces very fine oil bubbles.

SUMMARY OF THE INVENTION

An efficient artificial fog generator in accordance with the present invention includes, among other elements, an oil bath, one or more pipes located directly above the oil bath, filtering screens, air inlet for supplying air into each pipe, an enclosure or housing for substantially enclosing these elements, and fog outlet channels for the flow of fine oil bubbles out of the enclosure box to form the artificial smoke or fog. Each pipe includes one or more fine openings or holes on its surface. Normally, each pipe is confined at one or both ends using caps. As a result, an inflowing stream of air may only exit these pipes through the fine holes on the surface of these pipes. Due to the small cross section of these holes, the outgoing streams of air have a significantly high pressure. Because these holes are situated directly above the oil bath, these strong air jets spray the surface of the oil bath. The spraying of high pressured air in this manner onto the surface of the oil bath results in the generation of a significant cloud of fine oil bubbles from the surface of the oil bath.

One significant advantage of spraying an oil bath with a stream of high pressure air is the removal of a significant amount of fine oil bubbles, and only an insignificant amount of larger oil bubbles from the surface of the oil bath. This is in contrast with the prior art method of immersing fog nozzles in an oil bath, which resulted in a significant amount of relatively large oil bubbles being generated from the oil bath.

This method of spraying air onto the surface of the oil bath produces a significantly high ratio of fine oil bubbles to larger oil bubbles. As a result, the need for a large oil bath, large air pump, and a large enclosure box is eliminated. Further, with few large oil bubbles produced at the outset, the need for an excessively complex and expensive filtering system is greatly reduced. As a result, a fog generator in accordance with the present invention operates in an efficient manner to cut down the costs.

The invention also includes one or more filtering screens for further refining the produced oil bubbles. The filtering screens include fine openings for preventing larger oil bubbles from passing through. The oil that is prevented from passing through the screens gets caught by the filtering screens and drips back into the oil tank.

To further refine the oil bubbles, a solid baffle may also be used. The baffle is normally an "L" shaped plate of metal that is mounted directly below the fog outlets. The baffle blocks most of the passageway between the filtering screens and fog outlets. The flying oil bubbles must pass through the filtering screens and then pass the baffle to get to the fog outlets. As a result, only the finer oil bubbles are capable of reaching the fog outlets.

Both the baffle and the filtering screens are virtually maintenance free. This is in contrast with most of the prior art machines that need frequent maintenance. It is noted that maintenance costs add to the cost of using these machines.

The pipes that spray a high-pressured stream of air onto the oil bath are normally cylindrical with small holes oriented and positioned so that the air stream coming out of these holes is directly sprayed onto the oil bath. For maximum efficiency, the location of the pipes relative to the oil bath may be adjusted according to the pressure of air stream that flows through the pipes. If an air pump that generates one-third to three-quarters of a horsepower is used, the maximum efficiency may be achieved by placing the pipes a distance of about one-half to three quarters of an inch away from the oil surface of the bath.

The invention also includes an enclosure box or housing for enclosing most of the functional elements of the invention. The enclosing box may include an oil level sight plug for indicating the level of oil in the oil bath. Further, the housing includes an oil filler inlet for adding more oil to the oil bath. An air filter may also be provided for preventing debris or moisture from entering the pipes or the oil bath.

In addition, an air valve may be provided for preventing the input air stream from flowing into the pipes. The air valve is normally needed when the fog generator is used in studios that have their own air pump. Normally, these air pumps are located in a room other than the studio room where the fog generator is used. In this situation, a hose is used to connect the pump to the fog generator. This hose passes through the studio wall into the studio. As a result, the user of the fog generator does not have access to the air pump. The valve is used in this situation to shut off or turn on the flow of air into the fog generator. The air valve is not needed, however, when the user can directly control the operation of the pump. Due to the high efficiency of a generator in accordance with the present invention, a small air pump is sufficient for producing the desired result. Efficient and small air pumps, for example with ½ to ¾ horsepower, have yielded excellent quality artificial fog or smoke. These results have been achieved while saving on the cost of the pump and the required electricity to run these pumps.

The invention also includes one or more fog outlets to let the produced cloud of fine oil bubbles out of the enclosure box. Each fog outlet may be supplied with a cap for shutting the fog outlet off when not in use. Normally the fog outlets are short cylindrical channels located at the top or on the walls of the fog generator housing.

In accordance with an alternative embodiment of the invention, the air pump unit may be enclosed within the fog generator box. The resulting fog generator becomes even more compact. This alternative embodiment operates in a manner similar to the embodiment described above. Both embodiments are efficient and produce fine oil bubbles. The size of the enclosing housing may also be the same. The only difference is the need for a separate air pump unit in the first embodiment. With the alternative embodiment of the invention, the whole fog generator unit and the air supply unit are assembled in one small housing with dimensions of 11" by 7" by 5¾".

Accordingly, by placing the spraying pipes at a desired distance from the oil bath and spraying the oil bath with high-pressured streams or jets of compressed air, the goal of providing a compact, efficient, inexpensive and virtually maintenance-free artificial fog or smoke generator, that produces a cloud of fine oil bubbles, has been achieved.

Other objects, features and advantages of the invention will become apparent from a consideration of the following detailed description and the accompanying drawings.

BRIEF DESCRIPTION OF THE DRAWINGS

FIG. 1 shows an artificial fog or smoke generator in combination with an air pump, illustrating the principles of the invention;

FIG. 2 is a cross-sectional side view of the fog generator of FIG. 1, showing a spraying pipe and the air supply assembly, taken along line II—II of FIG. 1;

DETAILED DESCRIPTION

Figure 3:
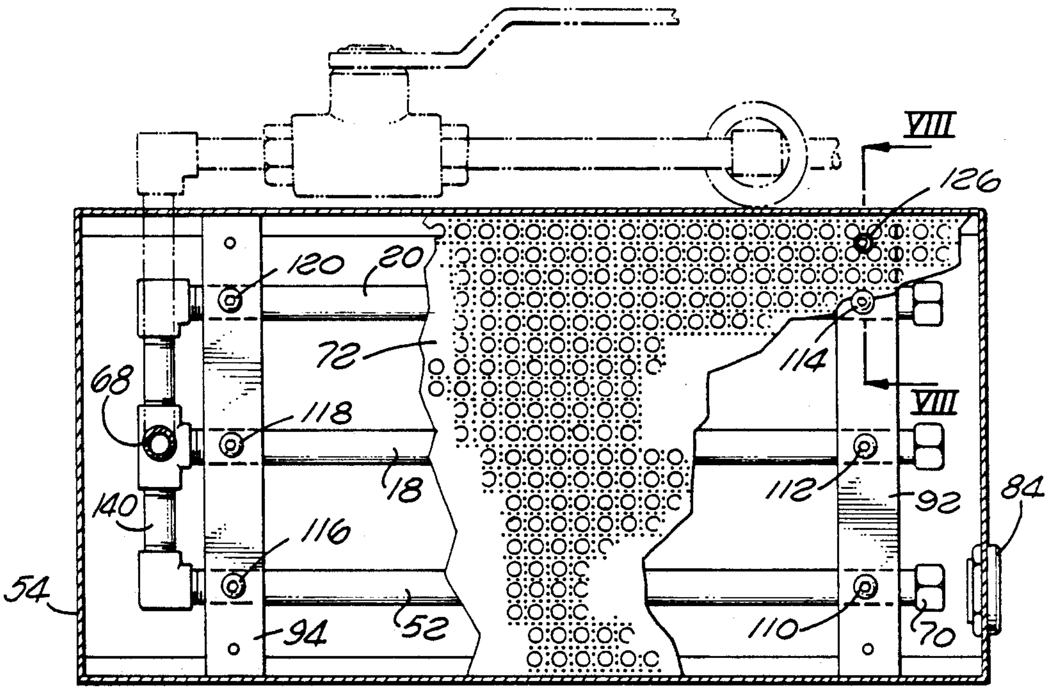
FIG. 3 is a cross-sectional top view of the fog generator of FIG. 1, taken along line III—III of FIG. 2, showing the spraying pipes and a filtering screen.

Referring more particularly to the drawings, FIG. 1 shows an air compressor 40 and an artificial fog generator unit 12. The fog generator 12 includes, among other elements, an oil bath 14 (see FIG. 2), three air jet pipes 52, 18 and 20 (see FIG. 3), air supply pipelines 22 and 68 for directing air into the pipes 52, 18 and 20, filtering screens 72 and 74 (see FIG. 4), and fog outlets 30, 82, 78 and 36. Compressed air is generated and supplied by air pump 40 and fed through pipeline 22 to spraying pipes 52, 18 and 20.

FIG. 2 is a cross-sectional side view of the artificial fog generator 12 of FIG. 1, taken along line II-88 of FIG. 1. As shown in FIG. 2, pipe 52 extends along the length of the housing 54, and includes several downwardly directed openings 56, 58, 60, 62, 64 and 66 along its length. Compressor 40 supplies a high pressure air through air supply pipeline 22, as shown in FIG. 1. The high pressure air flowing through pipeline 22 continues to flow to the main branch 68 that supplies air to the air jet pipes 52, 18 and 20 in the fog generator assembly 12. Because pipe 52 is sealed off by cap 70 at its end, the air stream that flows into pipe 52 must flow out of openings 56 through 66. The speed of the air jets that flow out of these openings is normally higher than the speed of air that flows through each individual spraying pipe due to the small cross-sectional area of these holes. The high speed jets of air that flow out of openings 56 through 56 spray into oil bath 14 and generate a cloud of fine oil bubbles which detach and fly out of the surface of oil bath 14. The generated cloud of oil bubbles is mostly composed of very fine oil bubbles. The produced cloud, however, also includes some undesirably larger oil bubbles. The larger oil bubbles are filtered out by filtering screens 72, 74 and 76. As the generated oil bubbles fly away from the surface of oil bath 14, they encounter the several filtering stages 72, 74 and 76. At each filtering stage, a substantial portion of the larger oil bubbles are prevented from passing through the fine openings on the surface of the filtering screen. The oil bubbles that get filtered out by the filtering screens collapse and drop back into the oil bath 14. The oil bubbles that pass through the filtering screens are normally very fine and have a high kinetic energy. To further refine the produced cloud of oil bubbles, an "L" shaped solid baffle 80 is mounted directly below the fog outlets.

With solid baffle 80 mounted directly below fog outlets 78 and 82 [and fog outlets 30 and 36, not shown], only those oil bubbles that fly above the baffle 28 and through screen 76 reach the enumerated fog outlets. More specifically, the oil bubbles that pass through all the filtering stages 72, 74 and 76 may get to the enumerated fog outlets only if they fly in the space above the solid baffle 80 with its vertical portion 28. This ensures that only those oil bubbles that have a light weight and high kinetic energy will reach the fog outlets 78, 82 30 and 36.

The portion of filtering screen 76 that is not blocked by baffle 80, 28 extends about one inch in height. Of course, this length could vary according to the exact need of the user.

While the fog generator is in operation, it may be desirable to determine the amount of oil that is left in the oil bath 14. Oil level sight plug 84, having a transparent center plate, is used for indicating the oil level in oil bath 14. If the user determines that more oil should be added to the oil bath 14, oil may be supplied through oil filler inlet 86. Oil filler cap 88 seals off filler inlet 86 during the normal operation of the fog generator 12. As shown in FIG. 1 and FIG. 2, the user may lift the fog generator assembly using handle 90 to shift it to the desired location or orientation.

FIG. 3 is a cut-away top view of the fog generator. As shown in FIG. 3, filtering screen 72 includes both fine and larger holes. The size of these holes may be varied for modifying the size of the output oil bubbles.

As shown in FIG. 3, spraying pipes 52, 18 and 20 are mounted directly above oil bath 14, and below the filtering screen 72. Transverse supporting numbers 92 and 94 are used for mounting these spraying pipes at the proper location. As shown in FIG. 3, the number 92 and 94 extend transversely across the width of the housing 54. As shown in FIG. 3, screws 110, 112, 114, 116, 118 and 120 are used to mount the pipes 52, 18 and 20 onto the support member 92 and 94. Further, filtering screen 72 is also supported by support members or beams 92 and 94 and is secured to them by screws 124 and 126.

Figure 4:
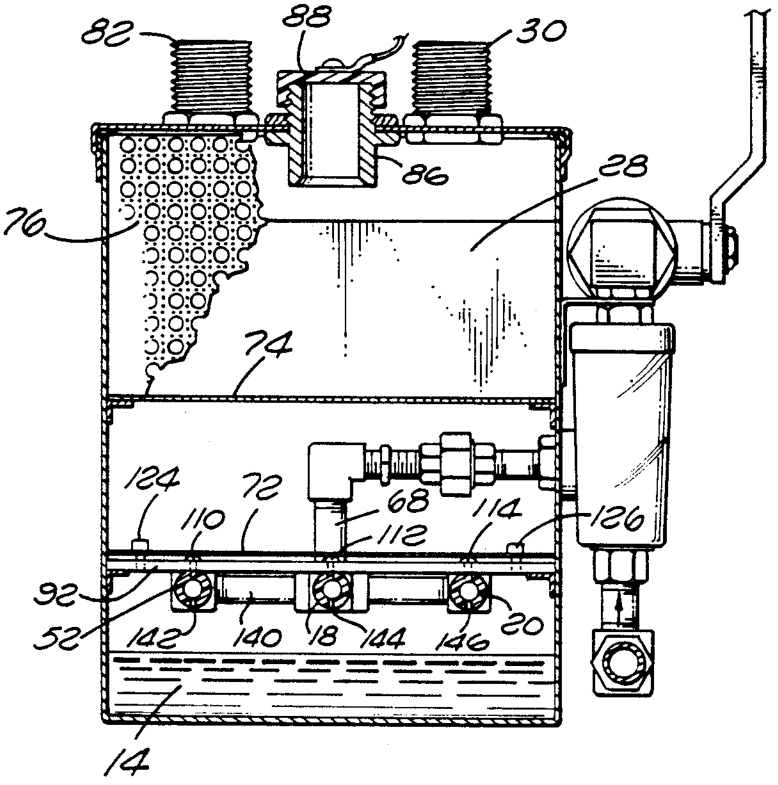
FIG. 4 is a cross-sectional rear view of the generator of FIG. 1 showing the spraying pipes and fog outlets, taken along line IV—IV of FIG. 3.

FIG. 4 is a cross-sectional rear view of the fog generator 12 of FIG. 1, taken along line IV—IV of FIG. 2. As shown, the air is supplied to pipes 52, 18 and 20 through the single air channel 68. The stream flowing through the tubing 68 is subdivided into three substantially equal streams of air flowing into pipes 52, 18 and 20. The air stream that flows out of tubing 68 flows into tubing 18 at a four-port fitting and from this fitting flows to pipes 20 and 52 via branch pipes including pipe 140. Each one of the pipes 52, 18 and 20 includes several downwardly directed holes or openings, such as openings 142, 144 and 146 on pipes 52, 18 and 20, respectively. As shown in FIG. 4, the relative diameter of these holes is small compared to the diameter of the pipes. As a result, with a limited number of these holes the velocity of the air jets that flow out of these openings is significantly higher than that of air streams that flow into the spraying pipes 52, 18 and 20. Further, since these high energy streams of air that come out of openings 142, 144 and 146 are directly sprayed onto the surface of the oil bath 14, a significant amount of fine oil bubbles are generated and fly away from the surface of oil bath 14.

Figure 5:
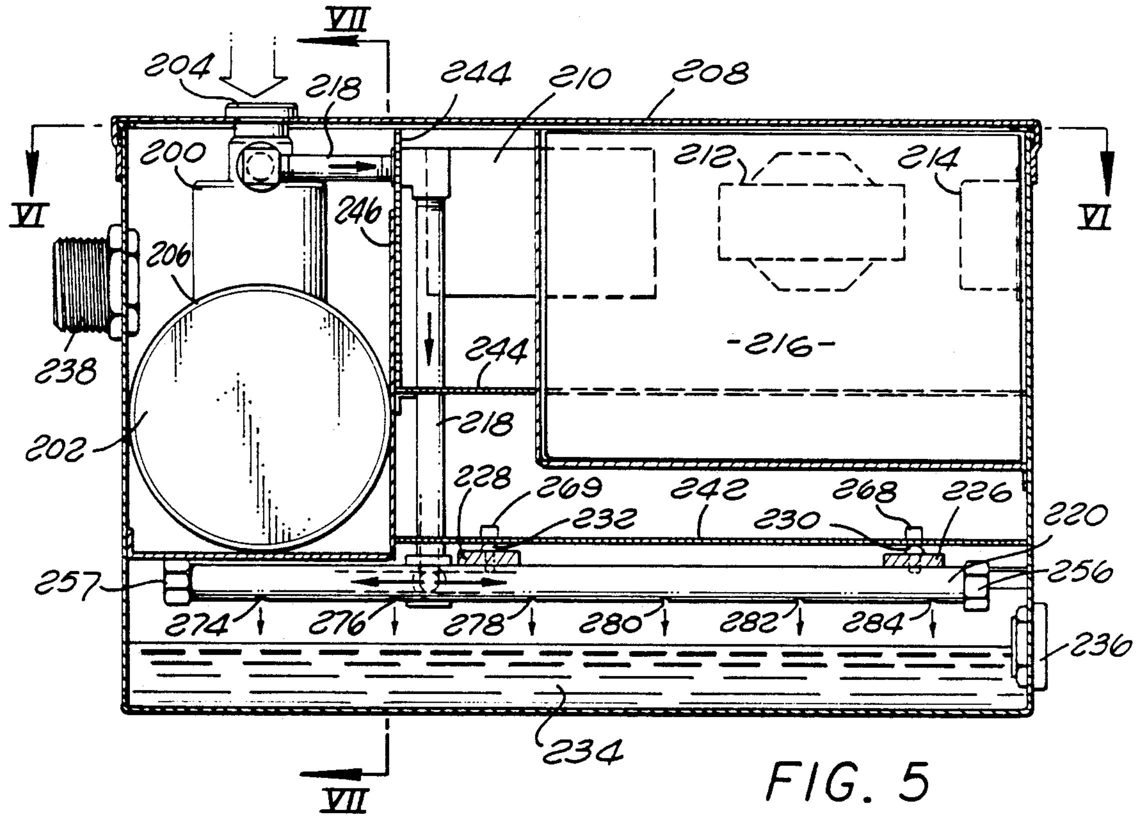
FIG. 5 is a side view of an alternative embodiment of the present invention showing the location of electrical and mechanical components of an air pump enclosed within the fog-generator housing.

FIG. 5 is a side view of an alternative embodiment of the present invention showing the location of electrical and mechanical components of an air pump 206 enclosed within the fog generator box 208, instead of the separate air pump of FIG. 1. As shown in FIG. 5, the motor 200, compressor 202 and the air inlet 204 that comprise the substantial portion of air pump 206 are all enclosed within the fog generator housing 208. The electrical components of air pump 206, namely battery charger 210, transformer 212, power inlet 214, and battery 216 are also enclosed within the fog generator housing 208. Air pump 206 draws the air in through the air inlet 204 and directs high pressure air into the inverse L-shaped tubing 218. The air stream that flows through tubing 218 is subdivided into three streams which flow into each of the tubes 220, 222, and 224. (See FIG. 6.) The air stream flowing through the pipes 220, 222 and 224 is then sprayed onto the oil bath 234 through the holes on the surface of the pipes 220, 222 and 224, for example, holes 274, 276, 278, 280, 282 and 284. Because these high energy streams of air that come out of these openings directly spray the surface of the oil bath 234, a significant amount of fine oil bubbles detach and fly away from the surface of oil bath 234. The generated oil bubbles then pass through screening filter 242, and then fly over the solid baffle 246 through screen 244 to get to the fog outlets 238 and 240. During this process, the larger oil bubbles are caught in the filtering screens 242 and 244, and therefore only the finer oil bubbles may pass through screens 242 and 244 and get to the fog outlet, as in the embodiment of FIGS. 1–4. The operation of the fog generator of FIG. 5 is virtually identical to the fog generator of FIG. 1, the only significant difference being that in the fog generator of FIG. 5, the air pump assembly 206 is also enclosed within the fog generator housing 208. Another difference, minor in nature, is the way that the tubing 218 is connected to the pipes 220, 222 and 224. As shown in FIG. 5, the tubing 218 is connected to the pipes 220, 222 and 224 at points intermediate the ends of these pipes. This is in contrast with the arrangement of FIG. 3, where the tubing 68 is connected to the ends of the pipes 52, 18 and 20. Experimental data evidence a more efficient operation with the arrangement of invention shown in FIG. 5.

Figure 6:
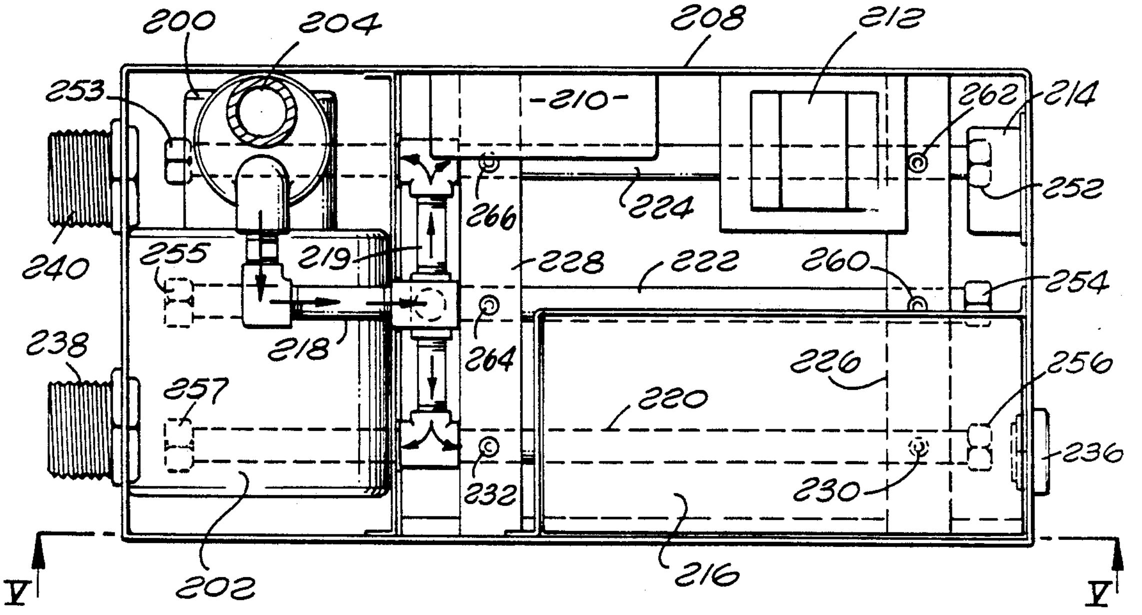
FIG. 6 is a top cross-sectional view of the generator of FIG. 6, taken along lines VI—VI of FIG. 5, showing more particularly the locations for the electrical and mechanical components of an enclosed air pump as well as the location for the air jet pipes.

FIG. 6 is a top view of the generator of FIG. 5 showing more particularly the location for the electrical and mechanical components of an enclosed air pump 206, as well as the location for the air jet pipes 220, 222 and 224. As shown in FIG. 6, the air is drawn into the air compressor 206 through the air inlet 204 and then fed into the tubing 218. Tubing 218 directs the flow of air to a five-port fitting at the bottom of the vertical tubing section 218, and from this fitting to pipe 222 and to air jet tubes 220 and 224 via short pipe or tubing sections including pipe 219. As shown, the air is coupled to the pipes 220, 222 and 224 somewhere along the length of these pipes 220, 222 and 224, thereby increasing the efficiency of the fog generator.

Because the air stream is fed into the pipes 220, 222 and 224 intermediate their ends, these pipes are capped off at both ends. As shown, pipe 220 is enclosed by caps 256 and 257, pipe 222 is enclosed by caps 254 and 255, and pipe 224 is enclosed by caps 252 and 253. As a result, the air stream that flows to each one of these pipes must flow out of these pipes only through the holes on the lower surface of the pipes, such as holes 274, 276, 278, 280 and 282 and 284 as shown in FIG. 5. Support beams or members 226 and 228 are used for supporting pipes 220, 222 and 224. As shown in FIG. 6, pipes 220, 222 and 224 are mounted on support beams 226 and 228 using the screws 230, 260, 262, 232, 264 and 266. These support beams are also used to support the filtering screen 242 as shown in FIG. 5 using the screws 268 and 269. Fog outlets 238 and 240 are used to direct the fine oil bubbles out of fog generator housing 208. Further, more fog outlets may be provided to allow the oil bubbles out of the fog generator housing 208.

By enclosing the mechanical and electrical components of air pump 206 within the air generator box 208, a more space-efficient fog generator unit is achieved, and ease of use and handling is enhanced.

Figure 7:
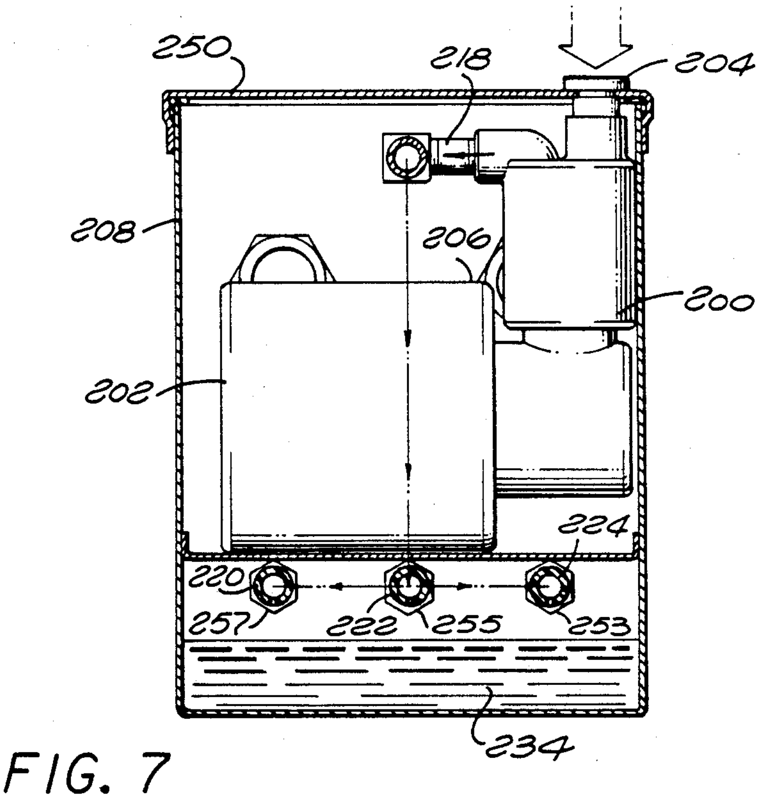
FIG. 7 is a rear cross-sectional view of the generator of FIG. 6, taken along lines VII—VII of FIG. 6, showing the air compressor, pipes and the oil bath.

FIG. 7 is a rear view of the generator of FIG. 6, taken along line VII—VII of FIG. 5, showing the air compressor 202, motor 200, the pipes 220, 222 and 224 and oil bath 234. As shown, the compressed air outlet of air pump 206 is fed into the tubing 218. The connection between the tubing 218 and the pipes 222 and 224 is not shown. As shown in FIGS. 5 and 7, the enclosing of the air pump 206 components does not interfere with operation of the fog generator device. As shown in FIG. 7, the compressor 202 and motor 200 are located directly above the spraying pipes 220, 222 and 224 and do not in any way interfere with the operation of these pipes. Further, as shown in FIG. 5, the compressor 202 and the motor 200 are located between the solid baffle 246 and the fog outlet, and therefore fill in space that would otherwise be wasted. Also, as shown in FIG. 5, the electrical components, namely, battery charger 210, transformer 212, electrical inlet 214, and battery 216 are enclosed within the casing above the filtering screen 244 and therefore do not interfere with the operation of the filtering stages. These components merely fill in the space that would otherwise be empty and wasted.

Figure 8:
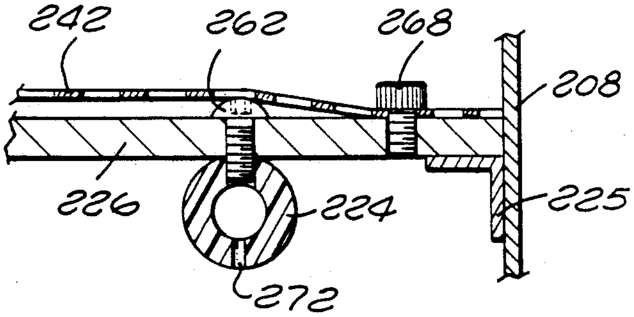
FIG. 8 is a partial cross-sectional side view of a generator in accordance with the present invention showing one filtering screen, tube support beam, and an air jet pipe.

FIG. 8 is a cross-sectional partial side view taken along line VIII—VIII of FIG. 3, and showing the filtering screen 242, tube support beam 226, and air jet pipe 224. As shown, the pipe 224 is mounted from support beam 226 using the screw 262. Similarly, filtering screen 242 is mounted on support beam 226 using the screw 268. The beam 226 is mounted on the fog generator box 208 using the L-shaped bracket 225. As indicated, the diameter of opening 272 on the surface of pipe 224 is relatively small compared to the inner diameter of the pipe 224. With the opening being much smaller than the diameter of the pipe 224, the air stream flowing out of the opening 272 is at a much higher velocity than the air stream flowing into the pipe 224.

Concerning dimensions, the operative units disclosed include a housing which is 5½ inches wide, seven inches high and about 11 inches long. The housing normally weighs about 9 to 15 pounds. The air jet tubes were made of plastic and had an outer diameter of about ⅜-inch and an inner diameter of about ¼- to 5/16-inch. The air jet openings from the tubes were about 0.006 inch to 0.013 inch in diameter. Although these dimensions were operative, it is to be understood that significant departures from these dimensions could, of course, be employed. The diameter range of the openings on the surface of the filtering stages is about 1/32 to ⅛ of an inch.

In conclusion, it is to be understood that the foregoing detailed description and the accompanying drawings are illustrative of the principles of the invention. It is noted in passing that a fog generator in accordance with the present invention may include one or more spraying pipes. The pipes may have various lengths and varying number of holes on their surfaces. Further the pipes may extend along the length or width of the enclosure box, or alternatively, extend at an angle with respect to the walls of the enclosure box. The pipes may be made of plastic, rubber, or metal, and may be flexible, if desired. The cross-section of the openings on the surface of the pipes may vary according to the user's needs. For maximum operational efficiency the pipes may be located at a distance of one-half to three-quarter of an inch above the oil bath if a ½ horsepower pump is used. Alternatively, this distance may vary depending on the horsepower of the air pump used to supply air into the fog generator device. The generator may include one or more filtering stages. Each filtering stage may include a multitude of fine openings on its surface. The size of these holes may vary according to the needs in a particular application. The filtering screens may be made of a metal or an alloy thereof. Solid baffles may also be used to further refine the oil bubbles. The solid baffle may be "L" shaped, or alternatively, have an arc-like cross-section. The solid baffle may be made of plastic, rubber, a metal or an alloy thereof. The enclosure box may be metallic, or alternatively, made of plastic. The enclosing means may have a rectangular cross-section, or alternatively, have any other convenient geometry. The fog generator may include one or more fog outlets. Each fog outlet may have a circular cross-section, or alternatively, a rectangular cross-section or other convenient geometry. The fog outlet may extend beyond the walls of the enclosure box or be limited to these walls. Further, the length of the fog outlet channel may vary according to the user needs. Finally, an electronic remote control device may be mounted on the fog generator or compressor. With the use of this remote control device, the user may active or deactivate the fog generator from a distance. The remote control may also be used to control the volume of air that is supplied to the fog generator device, and to control a fan to direct fog. Alternative forms of values and other components may be used. Accordingly, the present invention is not limited to the system precisely as shown in the drawings and described in the detailed description.

What is claimed is:

1. An efficient artificial fog or smoke generator comprising:

an oil bath;

at least one pipe having fine openings directed toward said oil bath, said pipe being mounted above and adjacent said oil bath;

means for supplying a high pressure stream consisting solely of air into each said pipe for directing jets consisting only of air into said oil bath, to generate fine bubbles of oil;

filtering means for filtering out large oil bubbles;

housing means for enclosing said oil bath, pipes and filtering means; and fog outlet means for directing the generated cloud of fine oil bubbles out of said housing;

whereby the visual effect from the resultant oil bubble cloud is maximized and the amount of oil employed is minimized.

2. An efficient artificial fog generator as defined in claim 1 wherein said filtering means includes multiple layers of filtering screens.

3. An efficient artificial fog generator as defined in claim 2 wherein said filtering screens include fine holes having a diameter less than ⅛ of an inch through their surfaces.

4. An efficient artificial fog generator as defined in claim 1 wherein said filtering means includes a solid baffle for further retaining the oil bubbles and eliminating larger oil bubbles.

5. An efficient artificial fog generator as defined in claim 1 wherein said pipes are positioned one-half to three-quarters of an inch above the oil level for maximum efficiency.

6. An efficient artificial fog generator as defined in claim 1 wherein said housing means is made of metal and includes an oil level sight plug.

7. An efficient artificial fog generator as defined in claim 1 wherein said air supplying means includes an air filter.

8. An efficient artificial fog generator as defined in claim 1 wherein said enclosing means includes no other substantial air outlet except for said fog outlet means.

9. An efficient artificial fog generator as defined in claim 1 wherein said fog outlet means includes multiple outlets for letting the fog out in a plurality of directions; and wherein each said channel includes a cap for closing said channel if desired.

10. An efficient artificial fog generator as defined in claim 9 wherein said outlets are located on at least one side and the top of the enclosing means.

11. An efficient artificial fog generator comprising:

an oil bath;

means for spraying compressed air onto the surface of said oil bath;

means for supplying a high pressure stream consisting solely of air to said means for spraying the air onto the oil bath, to generate fine bubbles of oil;

filtering means for preventing large oil bubbles from exiting to the surrounding atmosphere;

housing means for enclosing said oil bath, spraying means and filtering means; and fog outlet means for directing the generated cloud of fine oil bubbles out of said enclosing means;

whereby the visual effect from the resultant oil bubble cloud is maximized and the amount of oil employed is minimized.

12. An efficient artificial fog generator as defined in claim 11 wherein said air supplying means is substantially enclosed by said enclosing means.

13. An efficient artificial fog generator as defined in claim 12 wherein said air supplying means includes an efficient motor operating at about one-third to three-quarter of a horsepower;

said air supplying means includes an air filter.

14. An efficient artificial fog generator as defined in claim 12 wherein said enclosing means has dimensions 11" by $5\frac{3}{8}$" by 7";

each said pipe is about 9 inches in length, $\frac{1}{2}$ inch in diameter.

15. An efficient artificial fog generator as defined in claim 11 wherein said filtering means includes three stages of filtering screen, each filtering screen having a multitude of fine holes on its surface.

16. An efficient artificial fog generator comprising:

an oil bath;

means for directing jets consisting solely of compressed air onto the surface of said oil bath, to generate fine bubbles of oil; said means including a plurality of plastic pipes having downwardly directed openings;

means for supplying a high pressure stream of air to said means for directing the air jets onto the oil bath; said means including an air compressor for supplying a high pressure stream of air to said pipes;

filtering means for preventing large oil bubbles from exiting to the surrounding atmosphere; said filtering means including a plurality of filtering screens and a solid baffle;

housing means for enclosing said oil bath, pipes, and filtering means; said enclosing means including a metallic rectangular housing;

fog outlet means for directing the generated cloud of fine oil bubbles out of said enclosing means;

whereby the visual effect from the resultant oil bubble cloud is maximized and the amount of oil employed is minimized.

17. A fog or smoke generator as defined in claim 16 wherein means are provided for mounting said air compressor within said housing, and wherein power supply means for said air compressor are provided and are also mounted within said housing.

* * * * *